(12) United States Patent
Reichen et al.

(10) Patent No.: US 10,154,910 B2
(45) Date of Patent: Dec. 18, 2018

(54) ARTICULATING DISC IMPLANT

(71) Applicant: DePuy Synthes Products, Inc., Raynham, MA (US)

(72) Inventors: Marc Reichen, Buren a. d. Aare BE (CH); Kurt Schmura, Mohnton, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 305 days.

(21) Appl. No.: 14/873,565

(22) Filed: Oct. 2, 2015

(65) Prior Publication Data
US 2016/0030192 A1 Feb. 4, 2016

Related U.S. Application Data

(63) Continuation of application No. 14/513,462, filed on Oct. 14, 2014, now Pat. No. 9,168,148, which is a
(Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/442* (2013.01); *A61F 2/46* (2013.01); *A61F 2/4611* (2013.01); *A61F 2/28* (2013.01); *A61F 2002/2835* (2013.01); *A61F 2002/3065* (2013.01); *A61F 2002/30245* (2013.01);
(Continued)

(58) Field of Classification Search
CPC ..................... A61F 2/4425; A61F 2002/30242
See application file for complete search history.

(56) References Cited

U.S. PATENT DOCUMENTS

| | | |
|---|---|---|
| 928,997 A | 7/1909 | Muller |
| 3,474,537 A | 10/1969 | Christensen |

(Continued)

FOREIGN PATENT DOCUMENTS

| | | |
|---|---|---|
| CN | 1620271 A | 5/2005 |
| CN | 1665459 | 9/2005 |

(Continued)

OTHER PUBLICATIONS

U.S.Provisional Application filed Sep. 14,2008 by Kenny Koay et al., entitled Variable Angle Compression Plate, U.S. Appl. No. 61/242,102.

(Continued)

*Primary Examiner* — Ellen C Hammond
(74) *Attorney, Agent, or Firm* — Baker & Hostetler LLP

(57) ABSTRACT

An intervertebral disc implant for use in the spine including a first part and a second part, wherein the first part and second part are configured as a joint prosthesis for the spine. The first part includes one of a concave or convex articulating surface and the second part includes one of the other concave or convex articulating surface. One of the concave or convex articulating surfaces is preferably elliptically shaped in at least one direction and does not match and is different than one of the other concave or convex articulating surfaces.

17 Claims, 10 Drawing Sheets

Related U.S. Application Data continuation of application No. 12/995,723, filed as application No. PCT/US2009/046442 on Jun. 5, 2009, now abandoned.

(60) Provisional application No. 61/059,024, filed on Jun. 5, 2008.

(51) Int. Cl.
*A61F 2/28* (2006.01)
*A61F 2/30* (2006.01)

(52) U.S. Cl.
CPC ............... *A61F 2002/30253* (2013.01); *A61F 2002/30654* (2013.01); *A61F 2002/30884* (2013.01); *A61F 2002/30934* (2013.01); *A61F 2230/0071* (2013.01); *A61F 2230/0076* (2013.01); *A61F 2310/00029* (2013.01); *A61F 2310/00179* (2013.01); *A61F 2310/00359* (2013.01)

(56) References Cited

U.S. PATENT DOCUMENTS

| | | | |
|---|---|---|---|
| 4,338,835 A | 7/1982 | Simons | |
| 4,459,766 A | 7/1984 | Linecker | |
| 4,759,766 A | 7/1988 | Buettner-Janz et al. | |
| 5,038,978 A | 8/1991 | Kolton et al. | |
| 5,140,877 A | 8/1992 | Sloan | |
| 5,207,529 A | 5/1993 | Bailey | |
| 5,251,521 A | 10/1993 | Burda et al. | |
| 5,425,767 A | 6/1995 | Steininger et al. | |
| 5,443,469 A | 8/1995 | Smith | |
| 5,443,482 A | 8/1995 | Stone | |
| 5,505,731 A | 4/1996 | Tornier | |
| 5,779,705 A | 7/1998 | Matthews | |
| 5,797,918 A | 8/1998 | McGuire et al. | |
| 5,899,941 A * | 5/1999 | Nishijima | A61F 2/4425 623/17.15 |
| 5,984,681 A | 11/1999 | Huang | |
| 5,993,463 A | 11/1999 | Truwit | |
| 6,013,078 A | 1/2000 | Lin | |
| 6,113,637 A * | 9/2000 | Gill | A61F 2/4425 623/17.15 |
| 6,168,598 B1 | 1/2001 | Martello | |
| 6,221,074 B1 | 4/2001 | Cole et al. | |
| 6,235,033 B1 | 5/2001 | Brace et al. | |
| 6,270,499 B1 | 8/2001 | Leu et al. | |
| 6,409,730 B1 | 6/2002 | Green et al. | |
| 6,443,954 B1 | 9/2002 | Bramlet et al. | |
| 6,467,919 B1 | 10/2002 | Rumsey et al. | |
| 6,524,314 B1 | 2/2003 | Dean et al. | |
| 6,613,053 B1 | 9/2003 | Collins et al. | |
| 6,629,998 B1 | 10/2003 | Lin | |
| 6,648,892 B2 | 11/2003 | Martello | |
| 6,684,741 B2 | 2/2004 | Blackston | |
| 6,695,844 B2 | 2/2004 | Bramlet et al. | |
| 6,849,093 B2 | 2/2005 | Michelson | |
| 6,890,334 B2 | 5/2005 | Brace et al. | |
| 7,004,629 B2 | 2/2006 | Shrader | |
| 7,060,097 B2 | 6/2006 | Fraser et al. | |
| 7,094,242 B2 | 8/2006 | Ralph et al. | |
| 7,163,540 B2 | 1/2007 | Martello | |
| 7,198,643 B2 | 4/2007 | Zubok et al. | |
| 7,198,644 B2 | 4/2007 | Schultz et al. | |
| 7,235,101 B2 | 6/2007 | Berry et al. | |
| 7,270,679 B2 * | 9/2007 | Istephanous | A61B 17/7052 623/17.11 |
| 7,326,248 B2 | 2/2008 | Michelson | |
| 7,331,995 B2 | 2/2008 | Eisermann et al. | |
| 7,494,507 B2 * | 2/2009 | Dixon | A61F 2/30767 623/17.14 |
| 7,524,326 B2 | 4/2009 | Dierks | |
| 7,597,713 B2 | 10/2009 | Baumgartner et al. | |
| 7,611,539 B2 | 11/2009 | Bouttens et al. | |
| 7,637,928 B2 | 12/2009 | Fernandez | |
| 7,637,955 B2 * | 12/2009 | Marik | A61F 2/4425 623/17.14 |
| 7,670,340 B2 | 3/2010 | Brivio et al. | |
| 7,883,513 B2 | 2/2011 | Ralph et al. | |
| 7,887,590 B2 | 2/2011 | Levieux | |
| 7,905,906 B2 * | 3/2011 | Krishna | A61F 2/4425 606/257 |
| 7,927,374 B2 * | 4/2011 | Duggal | A61B 17/1604 623/17.14 |
| 7,981,114 B2 | 7/2011 | Zander | |
| 8,016,889 B2 * | 9/2011 | Dixon | A61F 2/30767 623/17.14 |
| 8,038,716 B2 * | 10/2011 | Duggal | A61F 2/4425 623/17.14 |
| 8,097,036 B2 * | 1/2012 | Cordaro | A61F 2/4425 623/17.15 |
| 8,343,196 B2 | 1/2013 | Schneider | |
| 8,361,157 B2 | 1/2013 | Bouttens et al. | |
| 8,470,037 B2 | 6/2013 | Re et al. | |
| 8,551,093 B2 | 10/2013 | Roth et al. | |
| 8,574,268 B2 | 11/2013 | Chan et al. | |
| 8,668,726 B2 | 3/2014 | Martin | |
| 8,758,346 B2 | 6/2014 | Koay et al. | |
| 8,845,698 B2 | 9/2014 | Schneider | |
| 8,852,245 B2 | 10/2014 | Schneider | |
| 8,876,873 B2 | 11/2014 | Schneider | |
| 8,888,779 B2 | 11/2014 | Senn et al. | |
| 2002/0128712 A1 | 9/2002 | Michelson | |
| 2003/0135216 A1 | 7/2003 | Sevrain | |
| 2003/0171753 A1 | 9/2003 | Collins et al. | |
| 2003/0199876 A1 | 10/2003 | Brace et al. | |
| 2004/0019353 A1 | 1/2004 | Freid et al. | |
| 2004/0111161 A1 | 6/2004 | Treiu | |
| 2004/0176844 A1 | 9/2004 | Zubok et al. | |
| 2004/0243241 A1 * | 12/2004 | Istephanous | A61B 17/7052 623/17.14 |
| 2005/0018931 A1 | 1/2005 | Shrader et al. | |
| 2005/0033438 A1 | 2/2005 | Schultz et al. | |
| 2005/0055024 A1 | 3/2005 | James et al. | |
| 2005/0059973 A1 | 3/2005 | Dierks | |
| 2005/0107791 A1 | 5/2005 | Manderson | |
| 2005/0216086 A1 * | 9/2005 | Marik | A61F 2/4425 623/17.15 |
| 2005/0240272 A1 * | 10/2005 | Zubok | A61B 17/8033 623/17.15 |
| 2006/0052787 A1 | 3/2006 | Re et al. | |
| 2006/0064095 A1 | 3/2006 | Senn et al. | |
| 2006/0116676 A1 | 6/2006 | Gradel et al. | |
| 2006/0189991 A1 | 8/2006 | Bickley | |
| 2006/0229729 A1 | 10/2006 | Gordon et al. | |
| 2007/0112354 A1 | 5/2007 | Iwasaki et al. | |
| 2007/0191952 A1 * | 8/2007 | Bernero | A61F 2/4425 623/17.15 |
| 2007/0213729 A1 | 9/2007 | Lindemann et al. | |
| 2007/0270971 A1 * | 11/2007 | Trieu | A61F 2/4425 623/17.15 |
| 2008/0140130 A1 | 6/2008 | Chan et al. | |
| 2008/0183171 A1 | 7/2008 | Elghazaly et al. | |
| 2008/0195212 A1 | 8/2008 | Nguyen et al. | |
| 2008/0221623 A1 | 9/2008 | Gooch | |
| 2008/0221624 A1 | 9/2008 | Gooch | |
| 2008/0243253 A1 | 10/2008 | Levieux | |
| 2008/0300639 A1 | 12/2008 | Martin | |
| 2009/0062920 A1 * | 3/2009 | Tauber | A61F 2/4425 623/17.16 |
| 2009/0069894 A1 * | 3/2009 | Duggal | A61B 17/1604 623/17.16 |
| 2009/0120852 A1 | 5/2009 | Ellsworth et al. | |
| 2009/0326545 A1 | 12/2009 | Schaffhausen | |
| 2010/0057132 A1 | 3/2010 | Graham et al. | |
| 2010/0076496 A1 | 3/2010 | Fernandez | |
| 2010/0121324 A1 | 5/2010 | Tyber et al. | |
| 2010/0121325 A1 | 5/2010 | Tyber et al. | |
| 2010/0145397 A1 | 6/2010 | Overes et al. | |
| 2010/0160924 A1 | 6/2010 | Soliman | |
| 2010/0167240 A1 | 7/2010 | Benzon et al. | |

(56) References Cited

U.S. PATENT DOCUMENTS

| | | |
|---|---|---|
| 2010/0256638 A1 | 10/2010 | Tyber et al. |
| 2010/0256639 A1 | 10/2010 | Tyber et al. |
| 2010/0274296 A1 | 10/2010 | Appenzeller et al. |
| 2010/0312280 A1 | 12/2010 | Overes et al. |
| 2010/0312286 A1 | 12/2010 | Dell Oca |
| 2010/0324556 A1 | 12/2010 | Tyber et al. |
| 2010/0324684 A1* | 12/2010 | Eisermann ......... A61B 17/1642 623/17.15 |
| 2011/0022066 A1 | 1/2011 | Sevrain |
| 2011/0087331 A1 | 4/2011 | Reichen et al. |
| 2011/0118739 A1 | 5/2011 | Tyber et al. |
| 2011/0125153 A1 | 5/2011 | Tyber et al. |
| 2011/0137312 A1 | 6/2011 | Mantovani et al. |
| 2011/0160729 A1 | 6/2011 | Overes et al. |
| 2011/0172773 A1 | 7/2011 | Reichen et al. |
| 2011/0184470 A1 | 7/2011 | Gorek et al. |
| 2011/0213367 A1 | 9/2011 | Tyber et al. |
| 2011/0230884 A1 | 9/2011 | Mantzaris et al. |
| 2011/0230920 A1 | 9/2011 | Gorek et al. |
| 2011/0282398 A1 | 11/2011 | Overes et al. |
| 2012/0143262 A1 | 6/2012 | Jensen et al. |
| 2014/0180345 A1 | 6/2014 | Fernandez |
| 2015/0018889 A1 | 1/2015 | Schneider |

FOREIGN PATENT DOCUMENTS

| | | |
|---|---|---|
| CN | 101094618 A | 12/2007 |
| CN | 101102730 | 1/2008 |
| CN | 101340851 A | 1/2009 |
| CN | 101507652 A | 8/2009 |
| CN | 101677863 A | 3/2010 |
| CN | 102046105 | 5/2011 |
| CN | 102046111 | 5/2011 |
| CN | 102292043 A | 12/2011 |
| EP | 0330328 | 8/1989 |
| EP | 0809975 A2 | 12/1997 |
| EP | 1658816 | 5/2006 |
| EP | 1779794 | 5/2007 |
| EP | 2328520 B1 | 6/2014 |
| FR | 2718014 A1 | 10/1995 |
| JP | 54-118566 | 8/1979 |
| JP | S58-036544 A | 3/1983 |
| JP | 10-057399 A | 3/1998 |
| JP | 11-137585 | 5/1999 |
| JP | 2001-252283 A | 9/2001 |
| JP | 2001-520071 A | 10/2001 |
| JP | 2003-518408 A | 6/2003 |
| JP | 2006-514238 A | 4/2006 |
| JP | 2006-519671 A | 8/2006 |
| JP | 2008-510517 | 4/2008 |
| JP | 2010-527726 A | 8/2010 |
| JP | 2011-517591 | 6/2011 |
| JP | 2011-523580 | 8/2011 |
| KR | 10-2011-0106863 A | 9/2011 |
| KR | 10-2011-7015221 A | 9/2011 |
| WO | WO 1999/20195 A1 | 4/1999 |
| WO | WO 1999/47061 | 9/1999 |
| WO | WO 2000/38586 | 7/2000 |
| WO | WO 2000/69352 | 11/2000 |
| WO | 2004/008980 A1 | 1/2004 |
| WO | WO 2004/078049 | 9/2004 |
| WO | WO 2006/016384 | 2/2006 |
| WO | WO 2006/119092 | 11/2006 |
| WO | WO 2007/048038 | 4/2007 |
| WO | WO 2007/098288 | 8/2007 |
| WO | WO 2009/092907 | 7/2009 |
| WO | WO 2009/120852 | 10/2009 |
| WO | WO 2009/149371 | 12/2009 |
| WO | 2010/017357 A1 | 2/2010 |
| WO | 2010/028095 A1 | 3/2010 |
| WO | WO 2010/065855 A1 | 6/2010 |
| WO | 2011/085272 A1 | 7/2011 |
| WO | WO 2011/155931 | 12/2011 |
| WO | 2012/102726 A1 | 8/2012 |

OTHER PUBLICATIONS

U.S.Provisional Application filed Oct. 30, 2007 by Koay et al.,, U.S. Appl. No. 61/000,907.

U.S.Provisional Application filed Jul. 29, 2008 by Alberto Angel Fernandez.,entitled Variable Angle Locked Bone Plate, U.S. Appl. No. 61/084,281.

U.S.Provisional Application filed Aug. 13, 2007 by Jason S. Chan et al.,entitled Highly Versatile Variable Angle Bone Plate System, U.S. Appl. No. 60/955,506.

European Patent Application No. EP 10 19 4618: Extended European Search Report dated May 12, 2011, 6 pages.

International Patent Application No. PCT/US2009/038376: International Search Report dated Oct. 29, 2009, 4 pages.

International Patent Application No. PCT/US2009/046442: International Search Report and Written Opinion dated Oct. 7, 2009, 14 pages.

McKoy et al., "An Interlocking Screw for Fixation in Osteoporotic Bone", Internal Fixation in Osteoporotic Bone (An, Ed.), 2002, 237-241 (Chapter 20).

Rajasekaran et al., "Translaminar Facetal Screw (Magerl's) Fixation", Neurology India, Dec. 2005, 53(4), 5 pages.

* cited by examiner

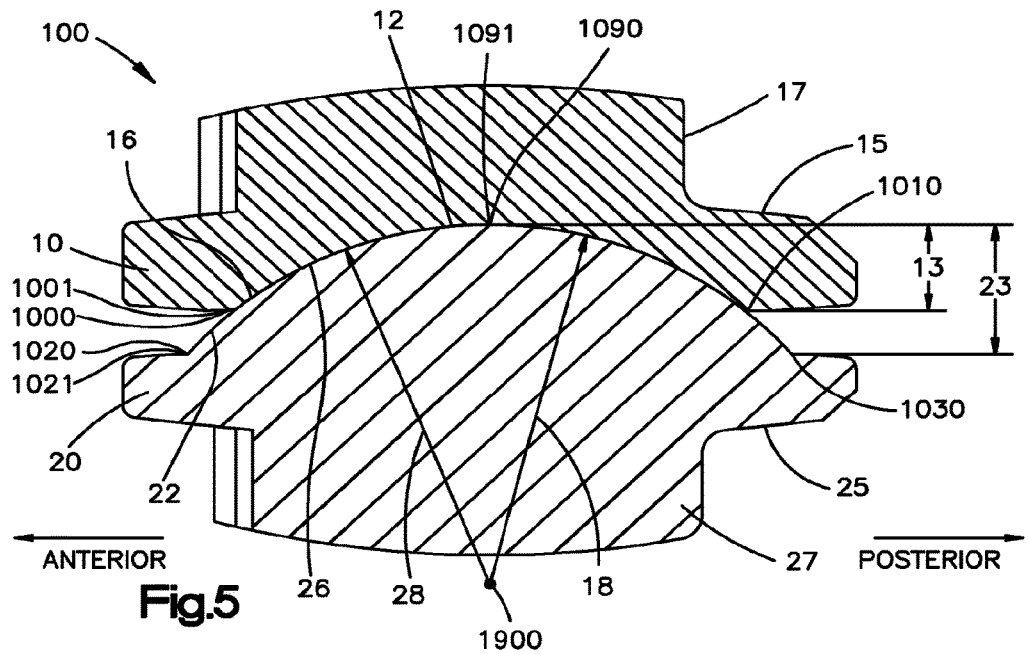
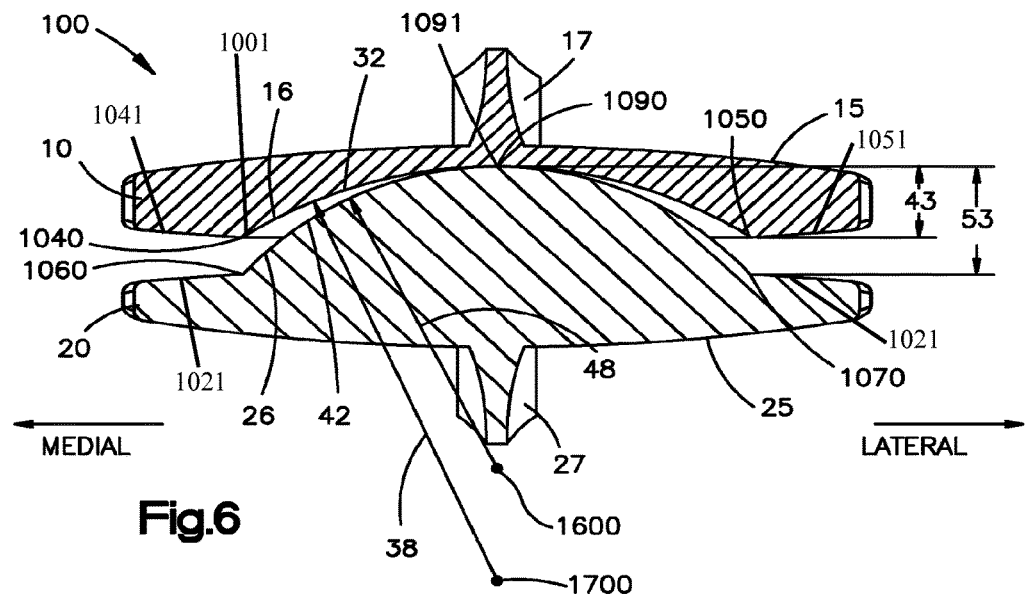

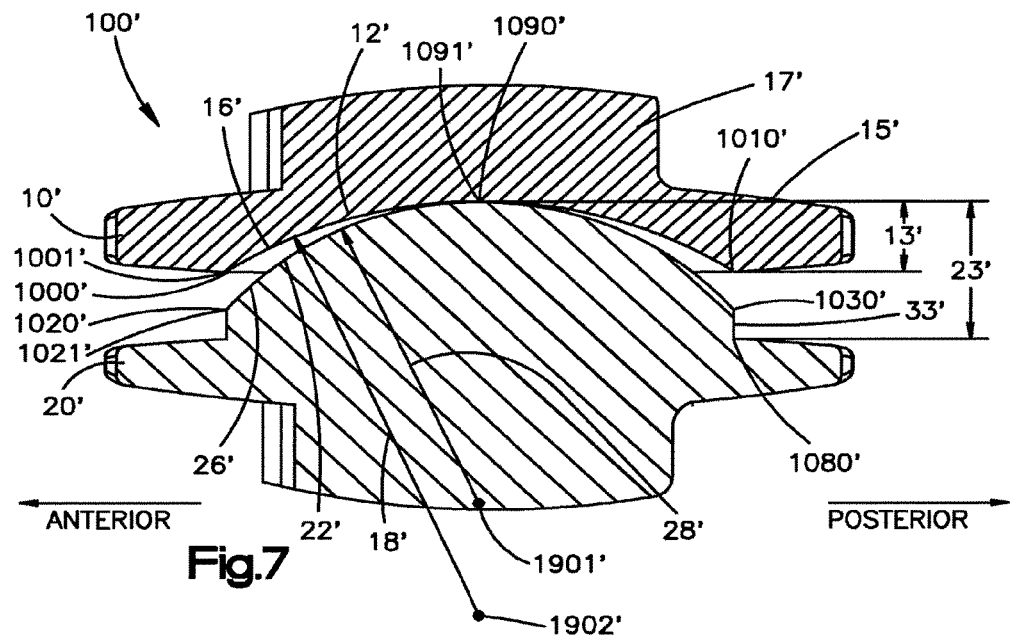
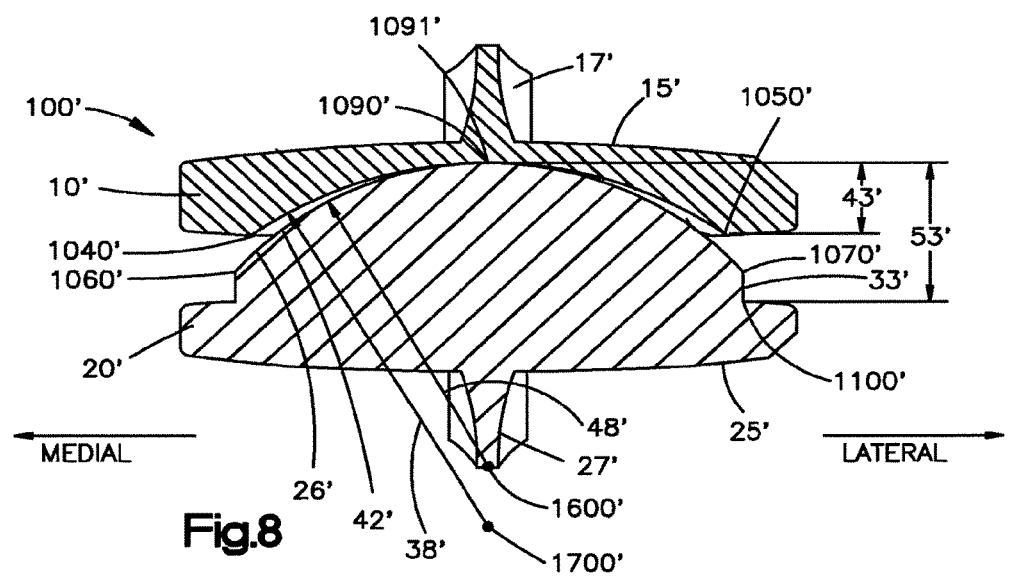

ARTICULATING DISC IMPLANT

CROSS-REFERENCE TO RELATED APPLICATIONS

This application is a continuation of U.S. application Ser. No. 14/513,462 filed Oct. 14, 2014, which is a continuation of U.S. application Ser. No. 12/995,723, filed Dec. 2, 2010, which is a National Stage of International Application No. PCT/US2009/046442, filed Jun. 5, 2009, which claims the benefit of U.S. Provisional Application No. 61/059,024, filed Jun. 5, 2008, the disclosures of which are incorporated herein by reference in their entireties for all purposes.

FIELD OF THE INVENTION

This invention relates to an implant, more specifically a joint prosthesis, more specifically an intervertebral implant, and even more specifically a joint prosthesis to replace a spinal disc.

BACKGROUND OF THE INVENTION

Due to general wear and tear, spinal discs can become damaged or dislocated giving rise to a problem commonly referred to as a "slipped disc". Intervertebral spinal discs lie between adjacent vertebrae in the spine. Each disc forms a cartilaginous joint allowing slight movement of the vertebrae and acting as a ligament to hold the vertebrae together. In the past, damaged discs were treated by removing the disc and packing the space with bone chips to promote fusion of the adjacent vertebrae. However, this method resulted in a loss of mobility in the patient's lower back. Another solution for treating damaged discs is to replace the damaged disc with a prosthetic disc implant. However, current prosthetic disc implants do not replicate the ranges of motion undertaken by healthy spinal vertebrae. Thus, there is a need for a prosthetic disc implant that can more closely approximate and permit the ranges of motion typically experienced by healthy spinal segments.

BRIEF SUMMARY OF THE INVENTION

The present invention is directed to an implant, more particularly a joint prosthesis, more preferably an intervertebral implant or joint prosthesis to replace a spinal disk. The intervertebral implant or artificial disc replacement device may have particular application in the cervical regions of the spine. In one embodiment, the intervertebral implant includes a first part and a second part wherein the first and second parts may be configured as a joint prosthesis preferably for the spine, and where the first part is moveable, preferably in situ, relative to the second part.

The first part has a surface for contacting the end plates of a first vertebrae and a first articulating surface, preferably having a continuously curved surface with no flat regions. The second part includes a surface for contacting the end plates of a second vertebrae and a second articulating surface, preferably having a continuously curved surface with no flat regions. The first articulating surface may contact, bear on, and be movable relative to the second articulating surface. The first articulating surface may be concave, and the second articulating surface may be convex.

The first articulating surface preferably is a different shape than the second articulating surface so that the two shapes do not match or nest, and the surfaces preferably will not contact over a majority or substantial majority of their surfaces. The first articulating surface preferably is elliptical in shape (i.e., a flattened circle or oval), preferably partially oblate ellipsoid and has a radius of curvature that varies, i.e., changes, along its length, preferably in at least the medial-lateral direction, although it may have an elliptical surface in other directions with a varying radius of curvature. The second articulating surface preferably is partially spherical in shape, with a constant radius of curvature that is the same in all directions. The radius of curvature of the first articulating surface in the medial-lateral direction (e.g., a first direction), although it may vary and change over its length, preferably has a different value than the radius of curvature of the second articulating surface in the same medial-lateral direction. The value of the first radius of curvature of the first articulating surface in the medial-lateral direction (although it may vary and change over its length), preferably may be greater than the value of the first radius of curvature of the second articulating surface in the same direction.

The second radius of curvature of the first articulating surface in the anterior-posterior direction (e.g., a second direction) may be relatively and substantially constant. The second radius of curvature of the first articulating surface in the anterior-posterior direction (e.g., the second direction) may have substantially the same value as the second radius of curvature of the second articulating surface in the same anterior-posterior direction. In this embodiment, where the radius of curvature is not the same in one direction but the same in a second direction, the first articulating surface may generally have a line of contact, or limited area of contact with the second articulating surface. Alternatively, the value of the second radius of curvature of the first articulating surface may be different than the value of the second radius of curvature of the second articulating surface in the same second direction. In this embodiment, where the radius of curvature is not the same in all directions the first articulating surface may have generally a point of contact or a limited area of contact with the second articulating surface.

The first and second articulating surfaces may be structured and arranged such that the first articulating surface undergoes a rolling motion relative to the second articulating surface in at least one direction, and preferably rolls on and along the articulating surface of the second part in at least one direction. During the rolling motion, the first part may axially rotate and roll on and along the second curved articulating surface. In this case, the instantaneous point of rotation of the first part moves on and along the second articulating surface in at least one direction.

The radius of curvature of the first and second articulating surfaces may be between about 1 mm and about 100 mm, and more preferably between about 1 mm and 30 mm. The first and second articulating surface may have an arc length between about 1.5 mm to about 30 mm.

The first articulating surface may have a depth, which is measured from the outer edge or the base point of the first articulating surface where the indentation or trough starts to the apex of the first articulating surface. The depth of the first articulating surface may range from about 0.5 mm to about 10 mm. The second articulating surface may have a height, which is measured from the outer edge or the base of the second articulating surface to the apex of the second articulating surface. The height of the second articulating surface may range from about 0.5 mm to about 10 mm. Preferably the value of the height of the second articulating surface is more than the value of the depth of the first articulating surface.

The surface of the first part for contacting the end plates of the first vertebrae preferably may be relatively flat and the surface of the second part for contacting the end plates of the second vertebrae may be curved. Alternatively, the surface for contacting the end plates of a vertebra of the first part may be curved, and additionally the surface for contacting the end plates of a vertebra of the second part may be relatively flat. The first part and the second part may be made of ceramic or other materials, now known or hereafter discovered. The first part may comprise a multi-piece assembly and the second part also may comprise a multi-piece assembly.

The first part and second part may be biased so that the apex of the first curved articulating surface tends to align with and contact the apex of the second curved articulating surface. That is the shape and geometry of the trough (concave surface) enables the articulating or bearing surface of the implant to return to a state of minimum energy (apex to apex) after the muscles no longer exert any forces on the spinal segment. The implant will tend to move back to its natural position wherein the portion of the convex surface in contact with the concave surface is located at the apex of the curvate concave articulating surface after lateral or rotation movement.

Another embodiment of the intervertebral implant includes an upper part including an upper surface sized and configured to contact an end plate of the first vertebra and a lower part including a lower surface sized and configured to contact an end plate of the second vertebra. The intervertebral implant further includes a convex articulating surface operatively associated with one of the upper and lower parts. The intervertebral implant also includes a concave articulating surface operatively associated with the other one of the upper and lower parts so that the upper part is moveable with respect to the lower part. The convex articulating surface may be shaped as a partial sphere with a constant radius of curvature that is the same in all directions. The concave articulating surface preferably may be shaped as a partial ellipse or oval with a radius of curvature that changes over the length of the curved concave articulating surface in at least one direction. The convex and concave articulating surface may be continuously curved with no flat regions.

The convex articulating surface has a first radius of curvature in a first direction and concave articulating surface has a first radius of curvature in the same first direction. The first radius of curvature of the convex articulating surface is preferably different than the first radius of curvature of the concave articulating surface in the same first direction. The first direction preferably may be the medial-lateral direction and the concave articulating surface preferably may be associated with the upper part.

The convex articulating surface may have a second radius of curvature in a second direction perpendicular to the first direction, preferably the anterior-posterior direction, and the concave articulating surface may have a second radius of curvature in the same second direction. The second radius of curvature of the convex articulating surface may be the same as the second radius of curvature of the concave articulating surface in the same second direction. Alternatively, the second radius of curvature of the convex articulating surface may be different than the second radius of curvature of the concave articulating surface in the same second direction. The convex articulating surface may have a radius of curvature in the anterior-posterior direction and the medial-lateral direction of about 1 mm to about 30 mm. The concave articulating surface may have a first radius of curvature in the anterior-posterior direction of about 1 mm to about 100 mm, more preferably about 1 mm to about 30 mm, and may have a second radius of curvature in the medial-lateral direction of about 1 mm to about 100 mm.

The convex articulating surface may have a constant radius of curvature in its lateral-medial direction, and in its anterior-posterior direction. Preferably, the concave articulating surface may have a radius of curvature that varies or changes along its surface in the medial-lateral direction, and preferably has a constant radius of curvature in its anterior-posterior direction. Alternatively, the concave articulating surface may have a radius of curvature that varies or changes along its surface in the anterior-posterior direction.

The concave articulating surface may indent a depth from its base to its apex, and the convex articulating surface may project a height from its base to its apex. The depth of the concave articulating surface may have a different value than the height of the convex articulating surface. The depth of the concave articulating surface preferably may have a value less than the value of the height of the convex articulating surface. The depth of the concave articulating surface is preferably between about 1.5 mm and about 2 mm, and the height of the convex articulating surface is preferably between about 2 mm and about 3 mm.

The convex articulating surface may have an arc length in the anterior-posterior direction and the medial-lateral direction of about 1.5 mm to about 30 mm. The convex articulating surface may have an arc length in the medial-lateral direction and the anterior-posterior direction of about 1.5 mm to about 30 mm.

The concave articulating surface may only contact the convex articulating surface over a limited area, preferably an area comprising less than 50% of the area of the concave articulating surface, more preferably an area comprising less than 25% of the concave articulating surface, and more preferably an area comprising less than 10% of the concave articulating surface. The convex articulating surface may form generally a line of contact or limited linear area of contact with the concave articulating surface. Alternatively, the convex articulating surface may form generally a point of contact or circular area of contact with the concave articulating surface that preferably is less than the area of contact for the embodiment that has the line or limited linear area of contact.

In another embodiment the implant includes an upper part including an upper surface sized and configured to contact bone, an end plate of an upper vertebra, a lower part including a lower surface sized and configured to contact bone, a convex articulating surface operatively associated with one of the upper and lower parts, a concave articulating surface operatively associated with the other one of the upper and lower parts so that the upper part is moveable with respect to the lower part, wherein one of the concave and convex articulating surfaces is elliptically shaped with a radius of curvature that varies in at least one direction and the other of the concave and convex surfaces is partially spherically shaped having a constant radius of curvature in the same at least one direction. Preferably the other of the convex and concave articulating surfaces is partially spherically shaped having a constant radius of curvature that is the same in all directions.

The intervertebral implant may further include a first joint member, the first joint member including one of the convex and concave articulating surfaces. The first joint member may further include a first projection or a first recess for engaging one of a first recess or a first projection formed in the lower part. The intervertebral implant may further include a second joint member. The second joint member may include the other one of the convex and concave articulating surfaces and one of a second projection and a second recess for engaging one of a second recess and second projection formed in the upper part.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the preferred intervertebral implant and/or spine prosthesis of the present application, drawings of the preferred embodiments are shown. It should be understood, however, that the application is not limited to the precise arrangement, structures, features, embodiments, aspects, and instrumentalities shown, and that the arrangements, structures, features, embodiments, aspects and instrumentalities shown may be used singularly or in combination with other arrangements, structures, features, aspects, embodiments and instrumentalities. In the drawings:

FIG. 5 is a cross-sectional view of the intervertebral implant of FIG. 3 in the anterior-posterior direction (sagittal plane).

FIG. 6 is a cross-sectional view of the intervertebral implant of FIG. 3 in the medial-lateral direction (coronal plane).

FIG. 7 is a cross-sectional view of a different embodiment of an intervertebral implant in the anterior-posterior direction (sagittal plane).

FIG. 8 is a cross-sectional view of the intervertebral implant of FIG. 7 in the medial-lateral direction (coronal plane).

DETAILED DESCRIPTION OF THE INVENTION

Figure 1:
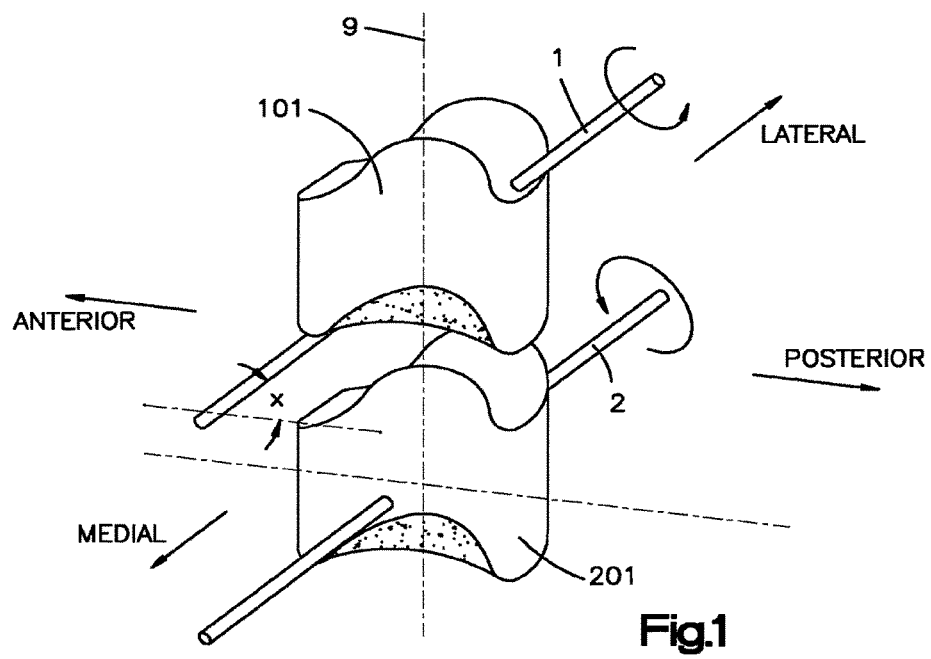
FIG. 1 is a schematically representation of the spine in the cervical region and the movement of adjacent vertebrae.

Certain terminology is used in the following description for convenience only and is not limiting. The words "right", "left", "lower", "upper", "bottom", and "top" designate directions in the drawings to which reference is made. The words "inwardly" and "outwardly" refer to directions toward and away from, respectively, the geometric center of the bone fixation element, instruments and designated parts thereof. The words, "anterior", "posterior", "superior", "inferior", "medial", "lateral" and related words and/or phrases designate preferred positions and orientations in the human body to which reference is made and are not meant to be limiting. The terminology includes the above-listed words, derivatives thereof and words of similar import.

FIG. 1 illustrates two adjacent cervical vertebrae, vertebra 101 and vertebra 201, which are located in the spine. Vertebrae 101 and 102 typically have a spinal disc (not shown) positioned between them that form a spinal segment that permits and facilitates movement of the vertebrae relative to one another. When a person moves their body, muscles exert pressure on vertebrae 101 and 201 causing them to move. In the cervical region when the vertebrae 101 and 102 move relative to each other they essentially rotate about axis 1, axis 2, or both axis 1 and 2. Referring to FIG. 1, axis 9 is the central axis of the spine and corresponds to the intersection of the medial-lateral and the anterior-posterior planes. In the cervical region, rotational axis 1 creates an angle X at the intersection of the axial plane, which includes axis 2. The value of angle X may be between about 10 degrees and about 60 degrees depending upon the location of the vertebrae in the cervical region of the spine. For example, axis 1 about which the cervical vertebrae C5 rotates about cervical vertebrae C6 is inclined about 45 degrees (X=45 degrees) with respect to the axial plane.

When a person bends their head forward, such as to look at their toes, or backwards, such as to look at the sky, the spine undergoes a motion known as flexion and extension, respectively. When the cervical spine undergoes pure flexion and pure extension, vertebrae 101 and 201 rotate about axis 2 and move in the sagittal plane.

When a person bends their head side to side, the cervical spine experiences a motion known as lateral bending. To describe this motion we need a fixed reference. In this case we chose the lower vertebrae of a motion segment (composed of inferior vertebrae, superior vertebrae and disc). Due to angle X that the cervical vertebrae makes with the axial plane, when a person bends their head from side to side, the spine will experience a combined motion between axial rotation and lateral bending. This is, during lateral bending, axial rotation is induced in the adjacent vertebrate. Therefore if the head is moved laterally it will induce axial rotation in the vertebrae. When cervical vertebrae 101 and 201 undergo pure lateral bending, the vertebrae rotate about both axis 1 and axis 2 to move in the coronal plane.

Finally, when a person twists their body or parts of their body, such as to turn their head left to right, the spine experiences a motion known as axial rotation. Due to angle X that the cervical vertebrae make with the axial plane, when a person twists their head, the spine experiences a combined motion between axial rotation and lateral bending. For example, during axial rotation, lateral bending is induced in the adjacent vertebrae. When the head undergoes pure axial rotation, cervical vertebrae 101 and 201 move about axis 1 and axis 2 so that the head will move in the axial plane as if rotating about reference axis 9.

Figure 2:
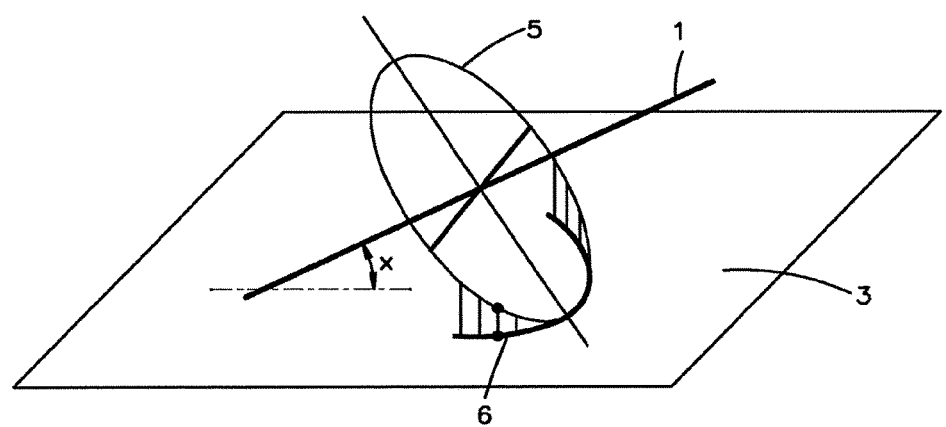
FIG. 2 is an illustration of a path of motion of cervical vertebrae about axis 1 of FIG. 1, which is projected onto the axial plane (the plane of axis 2 of FIG. 1).

FIG. 2 illustrates the motion experienced by vertebrae 101 and 201 from FIG. 1 during lateral bending of the spine. As shown in FIG. 1, during lateral bending, vertebrae 101 and 201 rotate about axis 1, creating a path of motion 5. When this path of motion 5 is projected onto axial plane 3, corresponding to the plane of axis 2, curved line 6 results. This curved line 6 corresponds to the path along which healthy vertebrae 101 and 201 move relative to one another when projected onto the axial plane 3. The line or path 6 is in the shape of an ellipse with a varying or changing radius of curvature.

Figure 3:
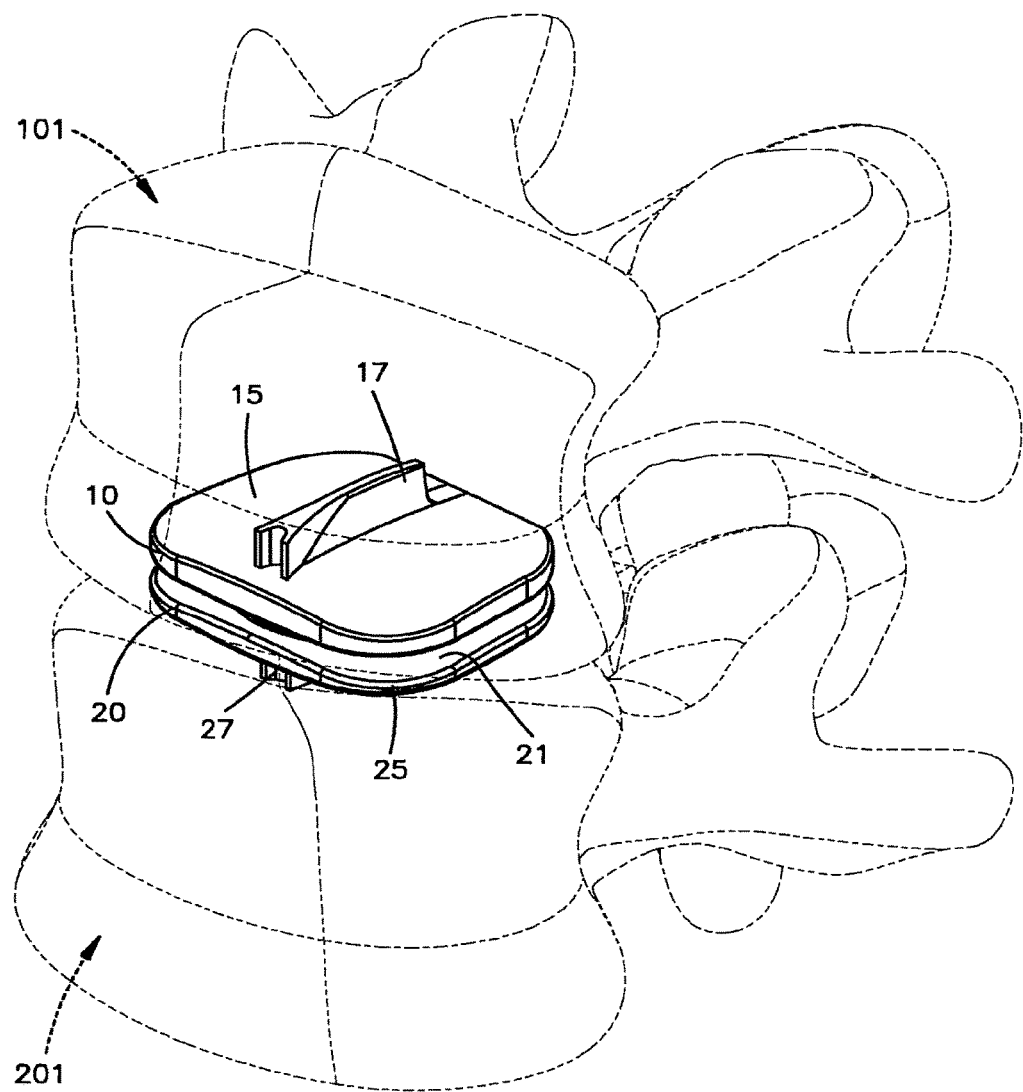
FIG. 3 is a perspective view of an intervertebral implant of the present invention attached to adjacent vertebrae.

FIG. 3 is an illustration of a prosthetic intervertebral implant 100 positioned between vertebrae 101 and 201 from FIG. 1. While intervertebral implant 100 is described for use in the spine, intervertebral implant 100 may have other uses and may be used as a prosthesis for other joints, such as, for example, the shoulder, elbow, wrists, hip, knee, ankle, toes and fingers. Intervertebral implant 100 preferably is for use in the cervical region of the spine. When used in the cervical region, intervertebral implant 100 preferably allows for the adjacent vertebrae (between which the implant is located) to experience the following ranges of motion, as described above: (i) about ±10 degrees during flexion and extension, (ii) about ±7 degrees during lateral bending, and (iii) about ±7 degrees during axial rotation. Alternatively, intervertebral implant 100 may be designed for other regions of the spine, such as, for example, the lumbar or thoracic regions. When the intervertebral implant 100 is designed for use in the lumbar region, the intervertebral implant 100 preferably allows for the spine to experience the following ranges of motion: (i) about ±10 degrees during flexion and extension, (ii) about ±7 degrees during lateral bending, and (iii) about ±10 degrees during axial rotation. Other ranges of motion may also be permitted by the implant.

FIGS. 3-10 and 13-15 illustrate exemplary embodiments of an intervertebral implant and more particularly a joint prosthesis for replacing a spinal disc. In general, such embodiments relate to an intervertebral implant 100, 100', 100", by way of non-limiting example, an intervertebral implant 100, 100', 100" for replacement of intervertebral discs or intervertebral fibro cartilage, which lies between adjacent vertebrae. While intervertebral implant 100, 100', 100" will be described as and may generally be used in the spinal regions (e.g., lumbar, thoracic, cervical), those skilled in the art will appreciate that intervertebral implant 100, 100', 100" may be used in other parts of the body. The invention may have other applications and uses and should not be limited to the structure or use described and illustrated. Generally, the same reference numerals will be utilized throughout the application to describe similar or the same components of each of the different embodiments of the intervertebral implant and the descriptions generally will focus on the specific features of the individual embodiments that distinguish that particular embodiment from the others.

Figure 4:
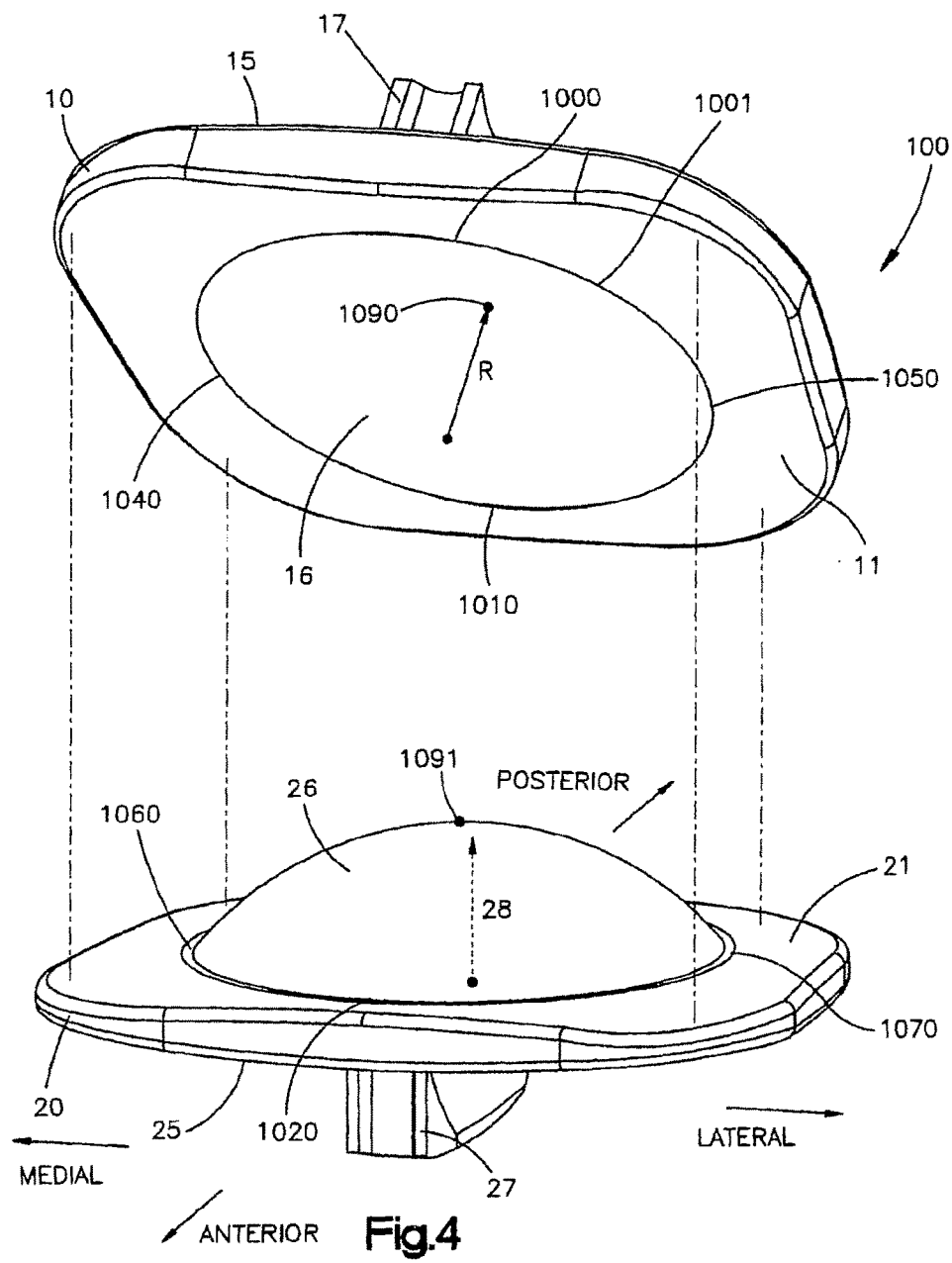
FIG. 4 is a perspective exploded view of the intervertebral implant of FIG. 3.

FIG. 4 illustrates one embodiment of an intervertebral implant according to the present invention. As shown in FIG. 4, intervertebral implant 100 preferably includes a first part 10 and a second part 20. Intervertebral implant 100 is designed so that in situ first part 10 moves relative to second part 20. First part 10 and second part 20 are configured to form a joint prosthesis to partially or fully replace a joint, such as, for example, a disc between two adjacent vertebrae. In the embodiment shown and illustrated in FIGS. 4-6, intervertebral implant 100 is intended to replace a spinal disc and preferably will permit the type and degree of motion generally experienced by healthy, adjacent cervical vertebrae. Implant 100 is designed particularly for application in the cervical regions of the spine. First part 10 and second part 20 each have a surface for abutting against and preferably engaging the end plates of adjacent vertebrae. First part 10 and second part 20 each also have an articulating or bearing surface that preferably oppose, contact, bear on and move relative to each other.

While first part 10 and second part 20 are each illustrated as single piece assemblies, each of first part 10 and second part 20 may comprise a multi-piece assembly. Furthermore, as generally understood by one of ordinary skill in the art, first part 10 and second part 20 can be made from any number of biocompatible materials, including, but not limited to ceramic, CoCr, PEEK, partially porous PEEK components, polymers, allograft bone, autograft bone, metals and alloys, and/or combinations thereof now known or later discovered.

As shown in FIG. 3, first part 10 is preferably the top or upper part of the implant and engages the superior vertebrae. More particularly, first part 10 has a first surface 15 for contacting vertebra 101 that is relatively flat. In alternative embodiments, first surface 15 may be slightly curved or substantially curved. First part 10 may further include one or more keels 17 preferably disposed in the anterior-posterior direction to secure the first part 10 to vertebra 101. While in this embodiment keel 17 is illustrated as the means for securing first part 10 to vertebra 101, additional or alternative securing means or elements may be used, such as, for example, teeth, ridges, in-growth areas, or screws.

Figure 9:
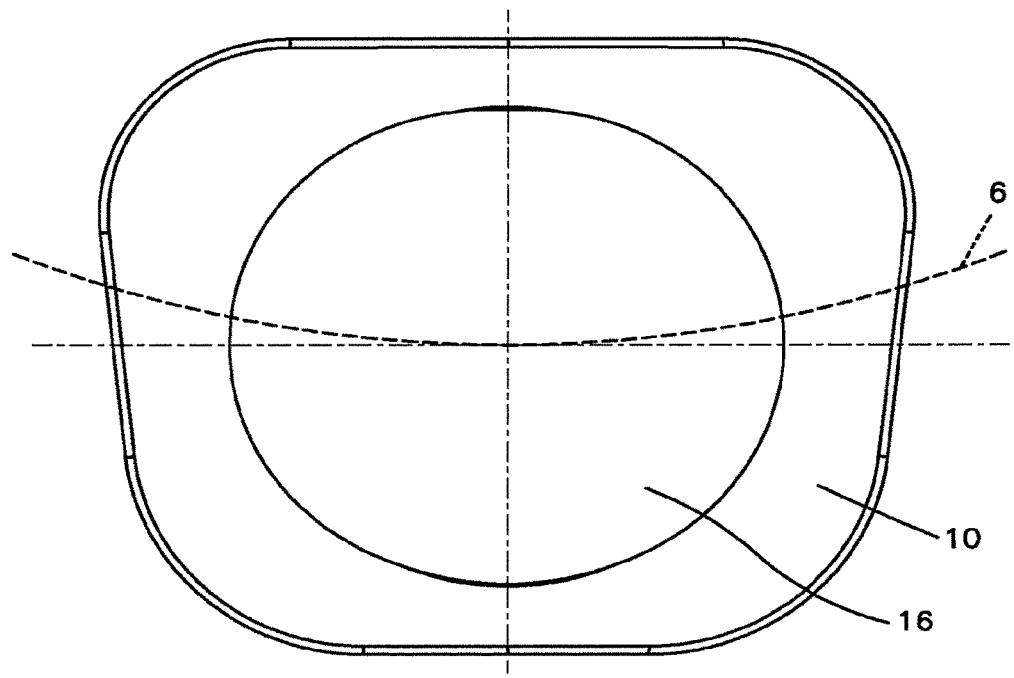
FIG. 9 is a bottom view of the top part of FIG. 3.

As shown in FIGS. 4 and 9, first part 10 also includes a first articulating surface 16, which is preferably a continuously curved surface with no flat portions. The first articulating surface 16 is preferably concave and preferably has the three dimensional shape of a partial oblate ellipsoid. In alternative embodiments, first articulating surface 16 may be a partial sphere and/or parabolically shaped. The preferred shape of the indentation or trough of the concave articulating surface in the anterior-posterior direction (saggital plane) is partially circular or spherical, having a constant radius of curvature. The preferred shape of the indentation or trough of the concave articulating surface 16 of first part 10 in the medial-lateral direction (coronal plane) is elliptical (oval-shaped) and preferably corresponds to dashed line 6 from FIG. 2. That is, in the preferred shape of the first articulating surface 16, the radius of curvature varies, e.g., changes, along the surface in the medial-lateral direction.

As shown in FIG. 4, second part 20 also includes a second articulating surface 26, which is preferably a continuously curved surface with no flat portions. The second articulating surface is preferably convex and has a three dimensional shape of a partial sphere. The radius of curvature of the second articulating surface is preferably constant and the same in all directions.

Accordingly, the first articulating surface 16 preferably does not match or correspond to the second articulating surface 26 so that the first curved articulating surface does not contact the second articulating surface over its entire surface or the entire surface of the second articulating surface. That is, for the embodiment of FIGS. 4-6, as a result of the partial elliptical or oval shape of the first articulating surface and the partial spherical shape of the second articulating surface, the two surfaces do not match, correspond or make contact over the entire areas of or substantially the entire areas of either of the articulating, bearing surfaces.

FIG. 5 illustrates a cross-sectional view of intervertebral implant 100 in the anterior-posterior direction along the sagittal plane. First articulating surface 16 preferably is indented and forms a trough in the horizontal plane of first part 10 that starts along the edge or line 1001. First articulating surface 16 has a first arc 12 in the anterior-posterior direction, measured from base point 1000 on the anterior side of edge 1001 to base point 1010 on the posterior side of edge 1001. Base points 1000 and 1010 are the end points of first articulating surface 16 in the anterior-posterior direction, and between which the surface is preferably continuously curved with no flat portions. First arc 12 of first articulating surface 16 preferably has a length between about 3 mm to about 30 mm, more preferably about 8 mm to about 15 mm, and more preferably about 10 mm to about 14 mm.

As shown in FIG. 5, first articulating surface 16 has a first radius of curvature 18 in the anterior-posterior direction, preferably between about 1 mm and about 30 mm, more preferably between about 5 mm and about 10 mm, and more preferably about 7.5 mm. Preferably, first radius of curvature 18 of first articulating surface 16 is substantially constant along the first arc 12 forming a partially circular or spherical surface in the anterior-posterior direction.

First part 10 further has a first depth 13 measured from base point 1000, 1010, where the indentation or trough of the concave articulating surface 16 starts at edge 1001, to apex 1090 of first articulating surface 16. First depth 13 preferably has a value between about 0.5 mm to about 5 mm, more preferably about 1 mm to about 2 mm, more preferably about 1.8 mm.

FIG. 6 illustrates a cross-sectional view of intervertebral implant 100 in the medial-lateral direction. First articulating surface 16 has a second arc 32 in the medial-lateral direction, measured from base point 1040 on the medial side of edge 1041 to base point 1050 on the lateral side of edge 1051. Base points 1040 and 1050 are the end points on opposite ends of first articulating surface 16 in the medial-lateral direction, and between which the surface is preferably continuously curved with no flat portions. Second arc 32 of first articulating surface 16 preferably has a length between about 3 mm to about 30 mm, more preferably about 10 mm to about 20 mm, and more preferably about 10 mm to about 15 mm.

As illustrated in FIG. 6, first articulating surface 16 preferably has a second radius of curvature 38 in the medial-lateral direction. The second radius of curvature 38 of first articulating surface 16 preferably is between about 1 mm and about 100 mm. In this embodiment, second radius of curvature 38 varies or changes along the first articulating surface 16 in the medial-lateral direction. The second radius of curvature 38 of the first articulating surface 16 along second arc 32 preferably varies between about 1 mm and about 100 mm, more preferably about 7.5 mm to about 50 mm, and more preferably about 7.5 mm to about 30 mm.

Furthermore, first part 10 further has a second depth 43 measured from base point 1040, 1050, where the indentation or trough of the concave articulating surface 16 starts at edge 1001, to apex 1090 of first articulating surface 16. Second depth 43 preferably has a value between about 0.5 mm to about 5 mm, more preferably about 1 mm to about 2 mm, more preferably about 1.8 mm. Preferably, first depth 13 and second depth 43 are equal, and apex 1090 is located at the center of concave surface 16. Alternatively, first depth 13 may be different than second depth 43, and the apex 1090, or the deepest part of indentation 16 may be located off-center from the geometrical center of the indentation.

Referring to FIGS. 5-6, the value of first radius of curvature 18 of first articulating surface 16 is constant while the value of second radius of curvature 38 of first articulating surface 16 varies or changes along the length of the surface in the medial-lateral direction. While the value of the radius of curvature of the first articulating surface 16 in the second medial-lateral direction may vary, the value of first radius of curvature 18 of first articulating surface 16 may be different than and preferably less than the value of second radius of curvature 38 of first articulating surface 16 as shown in FIG. 6. Alternatively, the value of first radius of curvature 18 of first articulating surface 16 may be greater than, or equal to, the value of the second radius of curvature 38 of first articulating surface 16. Preferably, the length of first arc 12 of first articulating surface 16 is less than the value of second arc 32 of first articulating surface 16. Alternatively, the value of first arc 12 of first articulating surface 16 may be greater than, or equal to the value of second arc 32 of first articulating surface 16. Preferably, the value of first depth 13 is equal to the value of second depth 43. Alternatively, the value of first depth 13 may be greater than or less than the value of second depth 43.

As shown in FIGS. 3-4, second part 20 is preferably the bottom or lower part of the implant and engages the inferior vertebrae. Preferably, second part 20 has a first surface 25 for contacting vertebra 201 that is relatively flat. Alternatively, first surface 25 may be slightly curved or substantially curved. Second part 20 may further include one or more keels 27 disposed in the anterior-posterior direction to secure the second part 20 to vertebra 201. While in this embodiment keel 27 is illustrated as the means for securing second part 20 to vertebra 201, alternate or additional securing means or elements now known or later discovered may be used, such as, for example, teeth, ridges, bone in-growth areas, or screws.

Figure 10:
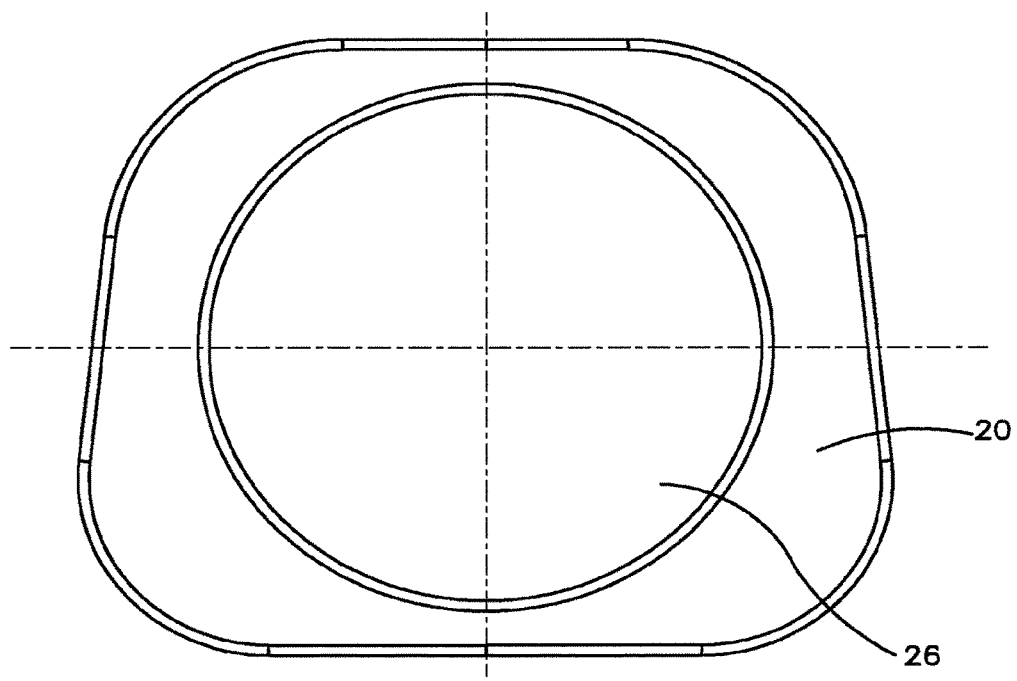
FIG. 10 is a top view of the bottom part of FIG. 3.

As shown in FIG. 4, second part 20 includes a second articulating surface 26 that preferably projects outward from second part 20, is convex and has the three dimensional shape of a partial sphere. FIG. 10 shows a top view of the second part 20 of FIG. 3, and in particular the convex second curved articulating surface 26, while FIGS. 4, 5, and 6 show a perspective side view, an anterior-posterior cross-section (sagittal plane) and a medial-lateral cross section (coronal plane) respectively.

As shown in FIG. 5, second articulating surface 26 has a first radius of curvature 28 in the anterior-posterior direction that is preferably constant and preferably is between about 1 mm and about 30 mm, and more preferably about 5 mm to about 10 mm, more preferably about 7.5 mm. Alternatively, the first radius of curvature 28 may vary along the second articulating surface 26 in the anterior-posterior direction.

Second curved articulating surface 26 has a first arc 22 in the anterior-posterior direction, measured from base point 1020 of edge 1021 on the anterior side to base point 1030 on the posterior side of edge 1021. Base points 1020 and 1030 are the end points of second articulating surface 26 in the anterior-posterior direction, and between which the surface is preferably continuously curved with no flat portions. First arc 22 of second articulating surface 26 preferably has a length between about 3.0 mm to about 30 mm, more preferably about 10 mm to about 15 mm, and more preferably about 13 mm to about 14 mm. The length of first arc 12 of first part 10 in the anterior-posterior direction preferably is less than the length of first arc 22 of second part 20 in the anterior-posterior direction.

Second part 20 further has a first height 23 measured from base point 1020, 1030, where the protrusion of convex articulating surface 26 starts at edge 1021, to apex 1091 of second articulating surface 16. First height 23 preferably has a value between about 2 to about 5, more preferably about 2 mm to about 3 mm, and more preferably about 2.5 mm.

As shown in FIG. 6, second articulating surface 26 has a second arc 42 in the medial-lateral direction, measured from base point 1060 on the medial side of edge 1021 to base point 1070 on the lateral side of edge 1021. Base points 1060 and 1070 are the end points on opposite ends of second articulating surface 26 in the medial-lateral direction, and between which the surface is preferably continuously curved with no flat portions. Second arc 42 of second articulating surface 26 preferably has a length between about 3.0 mm to about 30 mm, more preferably about 10 mm to about 15 mm, and more preferably about 12 mm to about 14 mm.

As illustrated in FIG. 6, second articulating surface 26 preferably has a second radius of curvature 48 in the medial-lateral direction. The second radius of curvature 48 of second articulating surface 26 preferably is between about 1 mm and about 30 mm, more preferably between about 5 mm to about 10 mm, and more preferably about 7.5 mm. Preferably, second radius of curvature 48 of second articulating surface 26 is constant or substantially constant in the medial-lateral direction. Alternatively, the second radius of curvature 28 may vary along the second articulating surface 26 in the medial-lateral direction.

Furthermore, second part 20 further has a second height 53 measured from base point 1060, 1070, where the protrusion of convex articulating surface 26 starts, to apex 1091 of second articulating surface 26. Second height 53 preferably has a value between about 2 mm to about 5 mm, more preferably about 2 mm to about 3 mm, and more preferably about 2.5 mm Referring to FIGS. 5-6, the value of first radius of curvature 28 of second articulating surface 26 preferably is the same as the value of second radius of curvature 48 of second articulating surface 26. The length of first arc 22 of second articulating surface 26 may be the same length as second arc 42 of second articulating surface 26. Alternatively, the length of first arc 22 of second articulating surface 26 may be greater than, or less than, the length of the second arc 42 of second articulating surface 26. Preferably, the value of first height 23 is equal to second height 53. Alternatively, the value of first height 23 may be greater than, or less than, the value of second height 53.

Preferably the value of first height 23 of second part 20 is greater than the first depth 13 of first part 10. Additionally, the second height 53 preferably is greater than the second depth 43 of first part 10. More preferably, the first height 23 is equal to the second height 53, which is greater than the first depth 13, and the second depth 43.

Furthermore, referring to FIGS. 5-6, the first articulating surface 16 does not match, correspond or nest with the second articulating surface 26 so that the first articulating surface 16 does not contact the second articulating surface 26 over substantially either first articulating surface 16 or second articulating surface 26. More specifically, first radius of curvature 18 of first articulating surface 16 preferably is constant and preferably has the same value as first radius of curvature 28 of second articulating surface 26 so that the first articulating surface 16 substantially matches and nests within the second articulating surface 26 in the anterior-posterior direction. However, the second radius of curvature 38 of first articulating surface 16 varies along its length forming the shape of an ellipse and has a different value than the second radius of curvature 48 of second articulating surface 26, so that the first articulating surface 16 preferably does not match the second articulating surface 26 in the medial-lateral direction. Preferably, second radius of curvature 38 of the first articulating surface 16 is greater than the second radius of curvature 48 of second articulating surface 26.

In the preferred embodiment, the convex, lower part 20 has a constant radius of curvature of about 7.5 mm in all directions and a height 23, 53 of about 2.5 mm, and an arc length of about 11 mm in all directions. In the preferred embodiment, the concave, upper part 10 in the anterior-posterior direction has a constant radius of curvature of about 7.5 mm, an arc length 12 of about 11 mm and a depth of about 1.8 mm, while in the lateral-medial direction has a radius 38 that varies along the length of arc 32, an arc length 32 of about 13 mm, and a depth of about 1.8 mm. Preferably the arc 32 is a partial ellipse with a the radius of curvature 38 in the medial-lateral direction that varies between about 1 mm and 100 mm.

The convex second articulating surface 26 may only contact the concave first articulating surface 16 over a limited area, less than the area of either the first articulating surface 16 or the second articulating surface 26. The value of this contact area may preferably comprise less than 50% of the area of first articulating surface 16 or second articulating surface 26. The value of this area more preferably may comprise less than 25% of first or second articulating surfaces, and even more preferably an area less than 10% of first or second articulating surfaces. Referring to FIGS. 5-6, first curved articulating surface 16 generally has a line or linear region of limited contact with second articulating surface 26 in the anterior-posterior direction. Preferably the first articulating surface 16 contacts the second articulating surface 26 generally along a line or region of limited length in the medial-lateral direction, but of greater length in the anterior-posterior direction. That is, the length of contact preferably is greater in the anterior-posterior direction than the length of contact in the medial-lateral direction. The limited contact length in the medial-lateral direction is shown in FIG. 6 where the convex articulating surface 26 contacts the concave articulating surface 16 along a band of limited length, and preferably at the apex 1090, 1091 when the vertebrae are in their natural position with no forces acting on them from the musculoskeletal framework.

When a person moves from side to side, inducing lateral bending, the muscles cause vertebrae 101 and 201 from FIG. 3 to move about axis 1 from FIG. 1. In turn, with intervertebral implant 100 inserted between adjacent vertebrae 101 and 201, the movement of the vertebrae causes first part 10 and second part 20, shown in FIGS. 3-6, to move relative to one another. In the embodiment of FIGS. 5-6, where the convex second articulating surface 26 substantially matches the concave first articulating surface 16 in the anterior-posterior direction, and the convex second articulating surface 26 does not match the concave first articulating surface 16 in the medial-lateral direction as a result of its elliptical shape and varying radius of curvature, the first part 10 will angularly rotate about the axis 1900 when undergoing flexion and extension.

Figure 14:
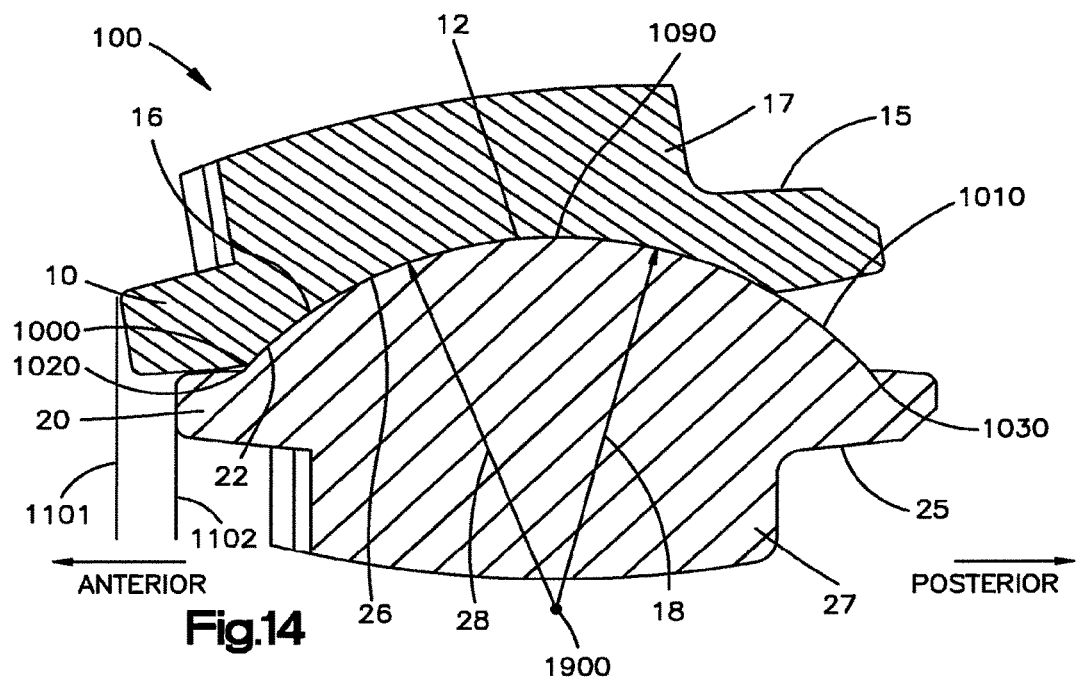
FIG. 14 is an illustration of the intervertebral implant of FIG. 5 with top part rotated in the anterior-posterior direction.

Referring to FIG. 14, when the first radius of curvature 18 of first articulating surface 16 equals the first radius of curvature 38 of second articulating surface 26, and the spine undergoes flexion, the upper or top first part 10 rotates about point 1900, which is the center of the radius of curvature 28 formed on the second articulating surface 26 in the second part 20. In the anterior-posterior direction, the first radius of curvature 28 of the convex second part 20 may be located outside of second part 20 (as shown in FIGS. 5 and 14) such that the concave first part 10 rotates about the axis of rotation 1900. Depending upon the geometry, the axis of rotation may also be located in the implant, and in the second part 20. As further illustrated in FIG. 14, when first part 10 rotates about second part 20 toward the anterior, this results in an induced translation whereby first part 10 slides on the second articulating surface 26 and shifts laterally toward the anterior with respect to the second part 20 from position 1101 to position 1102.

Figure 15A:
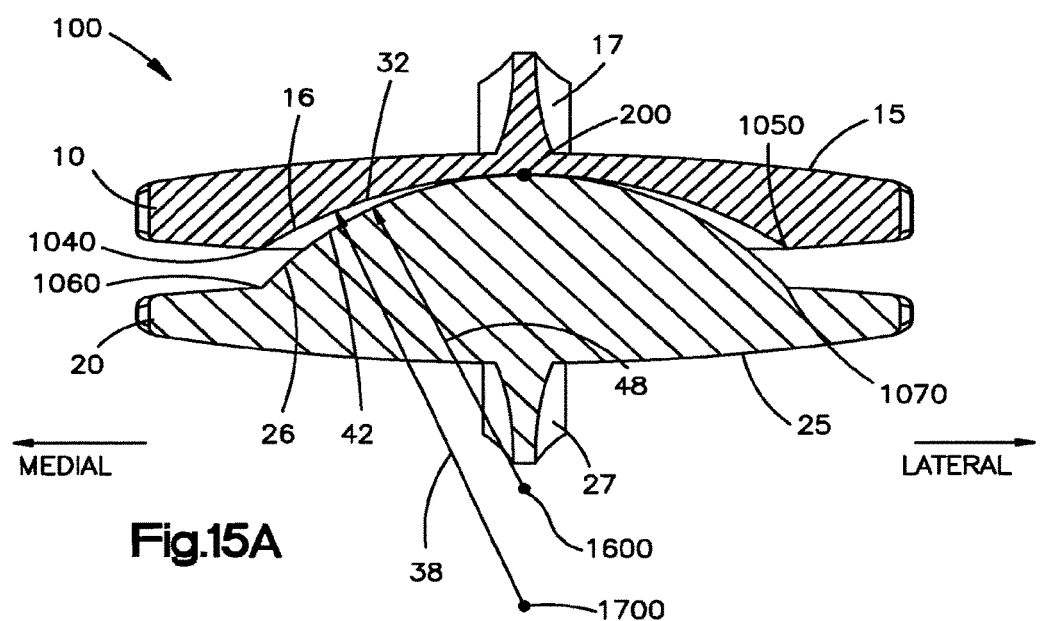
FIG. 15A is a cross-sectional illustration of the intervertebral implant of FIG. 6 with the top part centered in the medial-lateral direction.
Figure 15B:
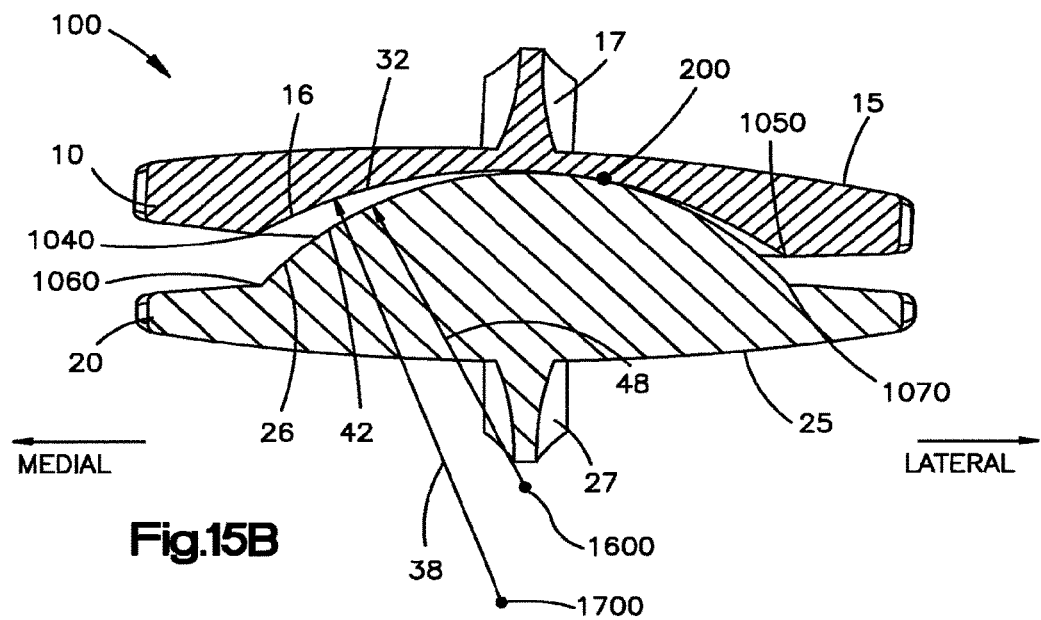
FIG. 15B is a cross-sectional illustration of the intervertebral implant of FIG. 6 with the top part rotated in the medial-lateral direction.
Figure 15C:
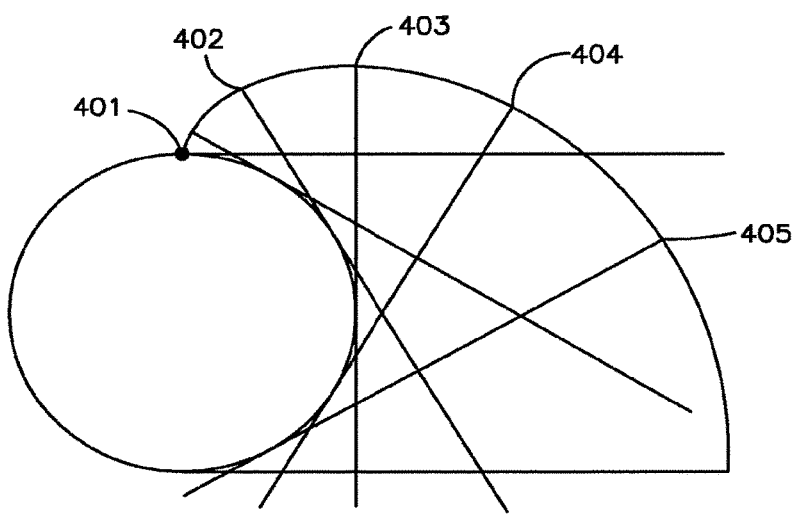
FIG. 15C is a schematic illustration of the path taken by the contact point 200 in FIGS. 15A-B during rotation of the top part of the intervertebral implant 100 of FIGS. 3-6 in the medial-lateral direction.

Referring to FIG. 6, the shape of the first articulating surface 16 is elliptical or oval in the medial-lateral direction, the second radius of curvature 38 of first articulating surface 16 varies or changes over the surface and is not equal to the second radius of curvature 48 of second articulating surface 26. Thus, when the spine undergoes lateral bending and the first part 10 moves in the coronal plane (medial-lateral direction) relative to the second part 20, the concave first articulating surface 16 rolls on the convex second articulating surface 26. Referring to FIGS. 15A, 15B, and 15C, when second articulating surface 26 rolls, the point of contact 200 and the axis of rotation of the first part moves and follows the path of convex articulating surface 26, thus rolling concave first articulating surface 16 over the convex second articulating surface 26. Referring to FIG. 15A, when no forces are exerted onto first part 10 and second part 20, such that first articulating surface 16 and second articulating surface 26 are in a state of equilibrium, and the spine is in an upright position with no flexion, extension, lateral bending or axial rotation, first part 10 is centered and aligned as shown in FIGS. 5-6 and 15A. As shown in FIG. 15A, when first part 10 and second part 20 are in a state of equilibrium, first part 10 is self-aligned with second part 20, meaning that point of contact 200 in the medial-lateral direction corresponds to apex 1090, 1091, and, the apex 1090 of first part 10 coincides with the apex 1091 of second part 20. However, when forces are exerted onto first part 10 and second part 20 during lateral bending, first part 10 and second part 20 move in the medial-lateral direction as shown in FIG. 15B, and contact point 200 and center of rotation of first part 10 moves to path point 404 shown in FIG. 15C. Thus, first part 10 rotates relative to second part 20, and rolls on and along the articulating surface of the second part.

As a result of the upper concave part 10 rolling along and on the lower, second articulating surface 26 of the second part 20 in the medial-lateral direction, such that the instantaneous axis of rotation moves along the surface 26 in the medial-lateral direction, there is no induced translation of the first part such that the upper concave part 10 undergoes a larger angular motion before it contacts the uncinate process. Thus, the implant 100 permits approximately 9.2 degrees of angular movement before the upper part contacts the uncinate process as opposed to the standard ProDisc-C sold by Synthes USA that generally permits about 2 degrees of angular rotation in the coronal plane before impingement with the uncinate process.

Another added benefit to the implant 100 is that the shape and geometry of the trough (concave surface) enables the bearing surface of the implant to return to a state of minimum energy (apex to apex) after lateral or rotational motion when the muscles no longer exert any forces on the spinal segment. That is the implant 100 will tend to move back to its natural position wherein the portion of the convex surface in contact with the concave surface is located at the apex of the curvate concave articulating surface after the muscles no longer exert a force on the spinal segment.

FIGS. 7-8 illustrate a second embodiment of an intervertebral implant 100'. Intervertebral implant 100' is similar to intervertebral implant 100 except for the differences noted herein. Preferably the first articulating surface 16' is concave, continuously curved with no flat spots, elliptically or oval shaped in both the anterior-posterior direction and the medial-lateral direction, and has a radius of curvature that varies over the surface in all directions. Preferably, the second articulating surface 26' is convex, continuously curved with no flat spots and is a partial sphere with a constant radius of curvature in all directions that is the same. Preferably the radius of curvature of the first articulating surface, although varying and changing over its surface, is larger than the radius of curvature of the second articulating surface. The radius of curvature of the concave articulating surface 16' in the anterior-posterior and the lateral-medial directions may be between about 1 mm and 100 mm, and preferably varies between 1 mm and 100 mm. The radius of curvature 18' and shape of the concave articulating surface in the anterior-posterior direction may be the same as the radius of curvature 38' and shape of concave articulating surface in the medial-lateral direction.

FIG. 7 illustrates a cross section of intervertebral implant 100' in the anterior-posterior direction, while FIG. 8 illustrates a cross section of intervertebral implant 100' in the medial-lateral direction. FIG. 7 corresponds to FIG. 5, except that unlike the embodiment shown in FIG. 5, the first radius of curvature 18' of first articulating surface 16' in the embodiment of FIG. 7 is not equal to the first radius of curvature 28' of second articulating surface 26' in the anterior-posterior direction. Intervertebral implant 100' in FIG. 8 is substantially similar to intervertebral implant 100 in FIG. 6, wherein the second radius of curvature 38' of the first articulating surface 16' is not equal to the second radius of curvature 48' of the second articulating surface 26' in the medial-lateral direction.

Referring to FIGS. 7-8, preferably, the value of first radius of curvature 28' of second articulating surface 26' is equal to the value of second radius of curvature 48' of second articulating surface 26'. Alternatively, the value of the first radius of curvature 28' of second articulating surface 26' may be less than or greater than the value of the second radius of curvature 48' of second articulating surface 26'.

The motion experienced by first part 10' relative to second part 20' in the medial-lateral direction is similar to the motion experienced by intervertebral implant 100 in the medial-lateral direction. Concave first part 10' will roll along the convex second part 20' in medial-lateral direction (when the spine undergoes lateral bending), and the axis of rotation of the first part 10' will be the point of contact between first part 10' and second part 20'. Preferably, first articulating surface 16' is concave and has, in both the anterior-posterior and medial-lateral directions, an elliptical or oval shape and the radii of curvature 18' and 38' change along the length of the first articulating surface 16'. Preferably, the second articulating surface 26' is convex and has constant radii of curvature 28' and 48' in both the anterior-posterior and medial-lateral directions.

Preferably the radii of the first articulating surface 16' do not match the radii of curvature of the second articulating surface 26' in any direction, including the anterior-posterior or medial-lateral directions. Preferably the concave first articulating surface 16' of the embodiment illustrated in FIGS. 7-8 contacts the convex second articulating surface 26' over a limited area, and preferably over an area of contact less than the area of contact of the embodiment illustrated in FIGS. 5-6. Preferably the area of contact of the first articulating surface 16' with the second articulating surface 26 is less than 50%, preferably less than 25%, and more preferably less than 10% of the convex second articulating surface 26'. Preferably the first articulating surface 16' contacts the second articulating surface 26' generally at a point or a region of limited contact that is generally circular or partially spherical and a smaller area than the area of second articulating surface 26'.

Furthermore, unlike intervertebral implant 100, intervertebral implant 100' has a projection or plateau 33' in second part 20, as shown in FIGS. 7-8. Projection 33' is measured from base point 1080' to end point 1030'. Projection 33' may have a value between about 0 mm to about 5 mm. Projection 33' provides the ability to produce different intervertebral implants by varying the length of projection 33'. By providing second parts 20' of different heights 33', different size implants can be assembled. For example, implants 100, 100' can be assembled into desired heights by supplying a kit with one or more first parts 10, 10' and 20, 20' with different size projections 33, 33' that may vary in 1 mm increments. Thus, for example, a first part 10, 10' may be supplied with projections 33, 33' of 0.5 mm, 1.5 mm, 2.5 mm, etc.

Figure 11:
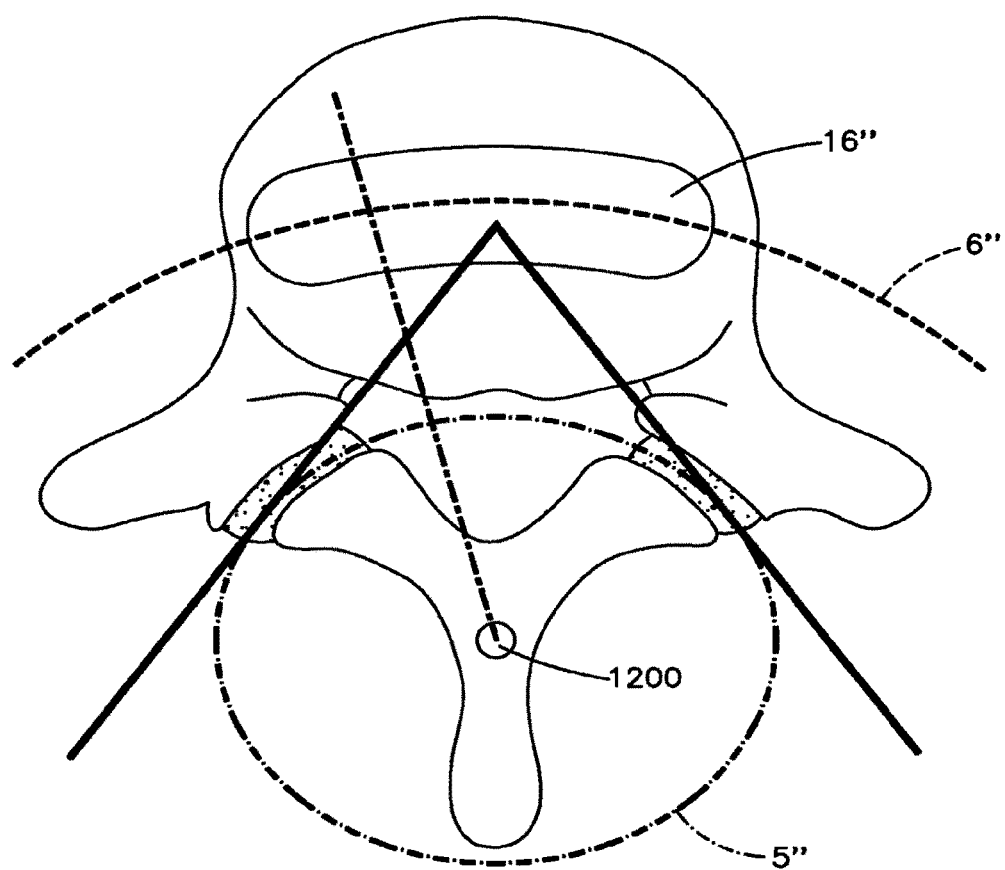
FIG. 11 is an illustration of a path of motion of a vertebra about axis 1 of FIG. 1 in the lumbar region of the spine.

FIG. 11 is illustrates the path of motion experienced by vertebrae 101 and 201 of FIG. 1 when vertebrae 101 and 201 are located in the lumbar region of the spine. Curved line 6" represents the motion that should be experienced by healthy lumbar vertebrae relative to one another. Unlike the cervical region, in the lumber region the path 6' of the lumber vertebrae in the axial plane is along the circumference of a circle, as opposed to an ellipse. More specifically, curved path 6" represents the path of the instantaneous axis of rotation of the upper lumbar vertebrae 101" along and over the lower lumbar vertebrae 102". Bean shape 16" represents a widened surface area projected along path 6" against and within the lumbar vertebrae.

Figure 12:
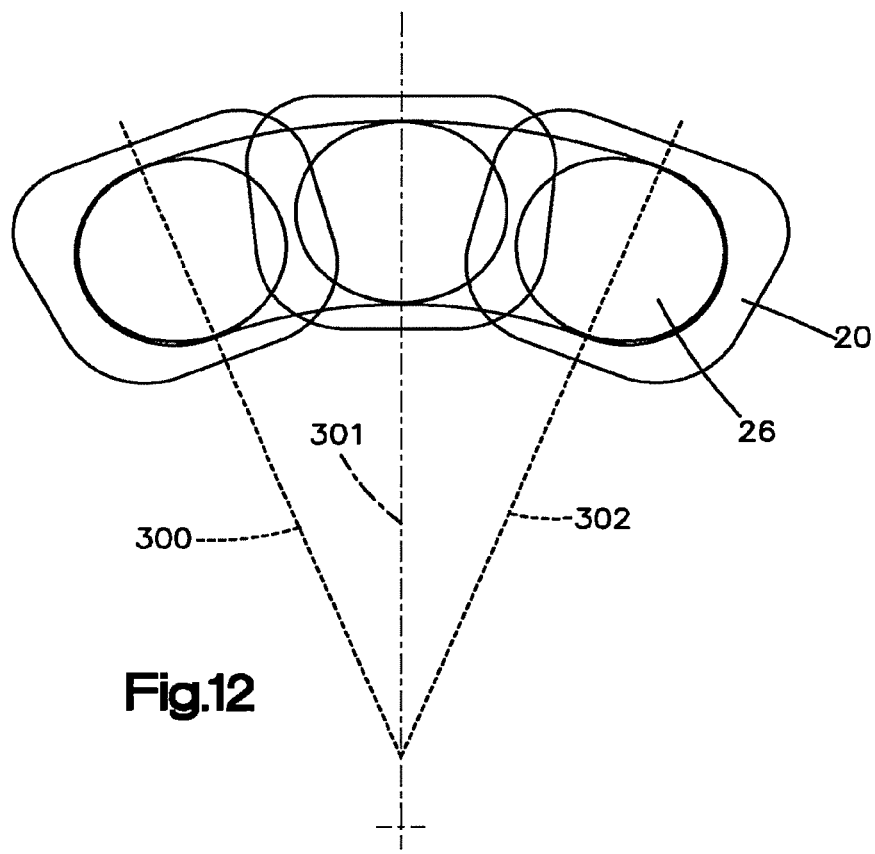
FIG. 12 is a schematic illustration of the bottom part of an intervertebral implant at different locations along the path of FIG. 11.

FIG. 12 illustrates where convex articulating surface 26 of second part 20 would be located in the lumbar region of the spine to contain the instantaneous axis of rotation of the upper adjacent lumbar vertebrae. More specifically, range lines 300 and 302 represent the maximum movement that the instantaneous axis of rotation would experience when projected on the lower lumbar vertebra. Based on this maximum range of movement of the axis of rotation, the shape of first articulating surface 16" for lumbar intervertebral implant prosthesis is created as shown in FIG. 13.

Figure 13:
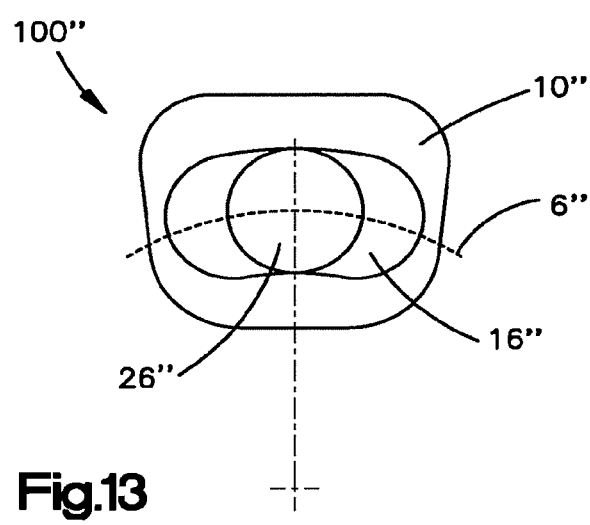
FIG. 13 is bottom view of the top part (with a projection of the bottom part) of another embodiment of an intervertebral implant designed to be implanted in the lumbar region of the spine.

FIG. 13 illustrates a bottom view of the top part 10" of an intervertebral implant 100" designed to be implanted in the lumbar region of the spine. Intervertebral implant 100" contains a first part 10" which contains a first curved concave articulating surface 16" as shown in FIG. 13. First articulating surface 16" has a bean like shape to accommodate the motion exerted on intervertebral implant 100" by the vertebrae located in the spine's lumbar region. In FIG. 13 the second convex articulating surface 26" of second part 20" is projected on the concave first articulating surface 16" as the circular section. As the lumbar vertebrae move, first curved concave articulating surface 16" moves on the convex second articulating surface 26". As can be seen in FIGS. 9 and 13, the first articulating surface 16" of intervertebral implant 100" of FIG. 13 has a much larger area for containing the second articulating surface 16" in the lumbar region than the area of first articulating surface 16 in FIG. 9. Therefore, due to this extended bean like shape of first articulating surface 16", intervertebral implant 100" preferably accommodates an axial rotation of up to ±10 degrees in the lumbar region, as opposed to ±7 degrees in the cervical region of the spine.

The shape of the first articulating surface in the medial-lateral direction may be shaped as a circle or sphere, or alternatively as an ellipse or oval with a radius of curvature that varies. The radius of curvature of the first, preferably concave, articulating surface is preferably between about 20 mm and about 100 mm. The concave surface 16" will be longer than the concave surface 16 or 16' and will also appear more curved due to its distance to the axis of rotation. The radius of curvature of the first, preferably concave, articulating surface in the lateral-medial direction is greater than the radius of curvature in the anterior-posterior direction, and preferably is greater than the radius of curvature of the second, preferably convex, articulating surface 26". The second articulating surface 26" preferably is spherical in shape and has a constant radius of curvature in all directions. The radius of curvature of the second, preferably convex, articulating surface in the lateral-medial direction is preferably different than the radius of curvature of the first, preferably concave, articulating surface in the lateral-medial direction so that the first articulating surface does not match, correspond or nest with the second articulating surface in the lateral-medial direction. Preferably, the concave articulating surface will roll on and along the convex articulating surface so that the instantaneous axis of rotation of the concave part about the convex part moves along the surface of the convex part.

It should be understood that the application is not limited to the precise arrangement, structures, features, embodiments, aspects, and instrumentalities shown, and that the arrangements, structures, features and instrumentalities shown may be used singularly or in combination with other arrangements, structures, features, aspects and instrumentalities. For example, the intervertebral implant 100 illustrated in the embodiment of FIGS. 5-6 may contain a projection 33 to increase the height of intervertebral implant 100. Additionally, for example, while the concave articulating surface has been shown and described as associated with the superior vertebrae and the convex articulating surface has been shown and described as associated with the inferior vertebrae, one of skill in the art could readily appreciate that the concave and convex surfaces can be switched and/or the convex surface can be elliptically parabollically shaped in one or more directions while the concave surface is partially spherical. Additionally, while the implant has been shown and described as having a first part and a second part, with each of first part and second part being a single monolithic piece, each of first and second part may be multiple pieces assembled together as well known in the art. Accordingly, first part or second part, or both, may comprise one piece to contact, engage, and secure to the vertebrae and another piece comprising the articulating or bearing surface, the two pieces being coupled together to form the first or second parts.

As will be appreciated by those skilled in the art, any or all of the components described herein may be provided in sets or kits so that the surgeon may select various combinations of components to form an implant and create a disc replacement system which is configured specifically for the particular needs/anatomy of a patient. It should be noted that one or more of each component may be provided in a kit or set. In some kits or sets, the same component or part may be provided in different shapes and/or sizes. The surgeon or staff may mix and match the first and second parts to create the implant before or during the procedure.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed:

1. An intervertebral implant for insertion into an intervertebral space between a first vertebra and a second vertebra, the implant comprising:
   a first part including a first outer surface configured to contact an end plate of the first vertebra, and a convex inner surface spaced from the first outer surface along a first direction, the convex inner surface having a first radius of curvature along a first plane defined along the first direction and a second direction, perpendicular to the first direction, and a second radius of curvature along a second plane defined along the first direction and a third direction, perpendicular to both the first and second directions;
   a second part including a second outer surface configured to contact an end plate of the second vertebra, and a concave inner surface that is spaced from the second outer surface along a direction opposite the first direction and that receives the convex inner surface so that the first part is moveable with respect to the second part, the concave inner surface having a first radius of curvature along a third plane, parallel to the first plane, and a second radius of curvature along a fourth plane, parallel to the second plane,
   wherein the first radius of curvature of the convex inner surface is different than the first radius of curvature of the concave inner surface, and the second radius of curvature of the convex inner surface is different than the second radius of curvature of the concave inner surface, and
   wherein at least one of the concave inner surface and the convex inner surface is continuously curved from a first end point to a second point, and the first radius of curvature of the one of the concave inner surface and the convex inner surface varies between the first and second end points.

2. The intervertebral implant of claim 1, wherein the second radius of curvature of the one of the concave inner surface and the convex inner surface varies.

3. The intervertebral implant of claim 1, wherein at least one of the first and second radii of curvature of the other one of the concave inner surface and the convex inner surface is constant.

4. The intervertebral implant of claim 1, wherein the first radius of curvature of the concave inner surface is greater than the first radius of curvature of the convex inner surface.

5. The intervertebral implant of claim 4, wherein the second radius of curvature of the concave inner surface is greater than the second radius of curvature of the convex inner surface.

6. The intervertebral implant of claim 1, wherein the first part is a lower part and the second part is an upper part.

7. The intervertebral implant of claim 1, wherein the concave inner surface is in the shape of a partial oblate ellipsoid.

8. The intervertebral implant of claim 7, wherein the convex inner surface is in the shape of a partial sphere.

9. The intervertebral implant of claim 1, wherein the concave inner surface only contacts the convex inner surface on an area comprising less than 50% of the area of the convex inner surface.

10. The intervertebral implant of claim 9, wherein the concave inner surface only contacts less than 25% of the convex inner surface.

11. The intervertebral implant of claim 9, wherein the concave inner surface only contacts less than 10% of the convex inner surface.

12. The intervertebral implant of claim 1, wherein the convex inner surface forms approximately point contact with the concave inner surface.

13. The intervertebral implant of claim 1, wherein the concave and convex inner surfaces are continuously curved with no flat portions.

14. The intervertebral implant of claim 1, wherein the second part includes an inner surface that is opposite the second outer surface and faces the first part, and the concave inner surface is (i) continuously curved in the first plane from the first end point on the inner surface to the second end point on the inner surface and (ii) continuously curved in the second plane from a third end point on the inner surface and to a fourth end point on the inner surface.

15. An intervertebral implant for insertion into an intervertebral space between a first vertebra and a second vertebra, the implant comprising:
   a first part including a first outer surface configured to contact an end plate of the first vertebra, and a convex inner surface spaced from the first outer surface along a first direction, the convex inner surface having a first radius of curvature along a first plane defined along the first direction and a second direction, perpendicular to the first direction, and a second radius of curvature along a second plane defined along the first direction and a third direction, perpendicular to both the first and second directions;
   a second part including a second outer surface configured to contact an end plate of the second vertebra, and a concave inner surface that is spaced from the second outer surface along a direction opposite the first direction and that receives the convex inner surface so that the first part is moveable with respect to the second part, the concave inner surface having a first radius of curvature along a third plane, parallel to the first plane, and a second radius of curvature along a fourth plane, parallel to the second plane,
   wherein the first radius of curvature of the convex inner surface is different than the first radius of curvature of the concave inner surface, the second radius of curvature of the convex inner surface is different than the second radius of curvature of the concave inner surface, and the first radius of curvature of one of the concave inner surface and the convex inner surface varies, wherein:
   the convex inner surface is (i) continuously curved in the first plane from a first end point to a second end point and (ii) continuously curved in the second plane from a third end point and a fourth end point; and the first part includes a first inner surface that is opposite the first outer surface and faces the second part, and includes a projection that spaces the first to fourth end points away from the first inner surface.

16. The intervertebral implant of claim 15, wherein one of the concave inner surface and the convex inner surface is continuously curved from a first end point to a second point, and the first radius of curvature of the one of the concave inner surface and the convex inner surface varies between the first and second end points.

17. The intervertebral implant of claim 15, wherein the concave and convex inner surfaces are continuously curved with no flat portions.

\* \* \* \* \*